United States Patent
Nappa et al.

(10) Patent No.: US 7,906,693 B2
(45) Date of Patent: Mar. 15, 2011

(54) PROCESSES FOR PRODUCING 2,3,3,3-TETRAFLUOROPROPENE, A PROCESS FOR PRODUCING 1-CHLORO-2,3,3,3-PENTAFLUOROPROPANE AND AZEOTROPIC COMPOSITIONS OF 1-CHLORO-2,3,3,3-TETRAFLUOROPROPENE WITH HF

(75) Inventors: Mario Joseph Nappa, Newark, DE (US); Velliyur Nott Mallikarjuna Rao, Wilmington, DE (US); Allen Capron Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 110 days.

(21) Appl. No.: 12/442,955

(22) PCT Filed: Oct. 31, 2007

(86) PCT No.: PCT/US2007/022991
§ 371 (c)(1),
(2), (4) Date: Mar. 26, 2009

(87) PCT Pub. No.: WO2008/054778
PCT Pub. Date: May 8, 2008

(65) Prior Publication Data
US 2010/0076231 A1    Mar. 25, 2010

Related U.S. Application Data

(60) Provisional application No. 60/855,513, filed on Oct. 31, 2006.

(51) Int. Cl.
C07C 17/00 (2006.01)
C07C 19/08 (2006.01)
(52) U.S. Cl. .......................................... 570/163; 570/124
(58) Field of Classification Search .................. 570/156, 570/257, 163, 124
See application file for complete search history.

(56) References Cited

U.S. PATENT DOCUMENTS 5,545,777 A * 8/1996 Morikawa et al. ............ 570/176
2006/0106263 A1 * 5/2006 Miller et al. .................. 570/155

FOREIGN PATENT DOCUMENTS

| EP | 0 436 903 A | | 7/2001 |
| WO | WO 91/01287 | * | 2/1991 |
| WO | 2008030442 | | 3/2008 |

OTHER PUBLICATIONS

Haszeldine R N et al.: "Addition of Free Radicals to Unsaturated Systems. Part XIII. Direction of Radical Addition to Chloro-1:1-Difluoroethylne" Journal of the Chemical Society. Letchworth, GB, 1957, pp. 2193-2196, XP009081235.

* cited by examiner

Primary Examiner — Jafar Parsa

(57) ABSTRACT

A process is disclosed for making $CH_2=CFCF_3$. The process involves contacting $CH_2ClCF_2CF_3$ with $H_2$ in a reaction zone in the presence of a catalyst including a catalytically effective amount of palladium supported on a support selected from chromium oxide, fluorinated chromium oxide, chromium fluoride, aluminum oxide, aluminum fluoride and/or fluorinated alumina, to produce $CH_2=CFCF_3$. The mole ratio of $H_2$ to the $CH_2ClCF_2CF_3$ fed to the reaction zone is between about 1:1 and about 4:1. Also disclosed is another process for making $CH_2=CFCF_3$ that involves (a) reacting $CH_2ClCF_2CF_3$ with $H_2$ in the presence of a catalytically effective amount of hydrogenation catalyst to form $CH_3CF_2CF_3$; and (b) dehydrofluorinating $CH_3CF_2CF_3$ from (a) to form $CH_2=CFCF_3$; and another process for making $CH_2=CFCF_3$ that involves (1) dehydrofluorinating $CH_2ClCF_2CF_3$ in the presence of a catalytically effective amount of dehydrofluorination catalyst to form $CHCl=CFCF_3$; and (2) hydrogenating $CHCl=CFCF_3$ from (1) in the presence of a hydrogenation catalyst including a catalytically effective amount of palladium supported on a support selected from chromium oxide, fluorinated chromium oxide, chromium fluoride, aluminum oxide, aluminum fluoride and/or fluorinated alumina to form $CH_2=CFCF_3$. Also disclosed is a process for making $CH_2ClCF_2CF_5$. This process involves reacting $CH_2ClF$ with $CF_2=CF_2$ in a reaction zone in the presence of a catalytically effective amount of an aluminum halide composition having a bulk formula of $AlCl_xBr_yF_{3-x-y}$, wherein the average value of x is 0 to 3, the average value of y is 0 to 3-x, provided that the average values of x and y are not both 0. Also disclosed is an azeotropic composition including $CF_3CF=CHCl$ and HF.

8 Claims, No Drawings

PROCESSES FOR PRODUCING 2,3,3,3-TETRAFLUOROPROPENE, A PROCESS FOR PRODUCING 1-CHLORO-2,3,3,3-PENTAFLUOROPROPANE AND AZEOTROPIC COMPOSITIONS OF 1-CHLORO-2,3,3,3-TETRAFLUOROPROPENE WITH HF

FIELD OF THE INVENTION

The present invention relates to processes that involve the production of halogenated hydrocarbon products comprising 2,3,3,3-tetrafluoropropene and/or 1-chloro-2,2,3,3,3-pentafluoropentane.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

2,3,3,3-Tetrafluoropropene ($CH_2$=$CFCF_3$, HFC-1234yf), having zero ozone depletion and low global warming potential, has been identified as a potential component in refrigerant blends (see PCT application published as WO 2006/094303). HFC-1234yf has been prepared by reaction of $CH_2ClC_2F_5$ with zinc in ethanol as reported by Haszeldine and Steele in Journal of the Chemical Society, pages 2193-2197 (1957). There is a need for new manufacturing processes for the product ion of HFC-1234yf.

SUMMARY OF THE INVENTION

The present invention provides a process for making $CH_2$=$CFCF_3$ (HFC-1234yf). The process comprises contacting $CH_2ClCF_2CF_3$ (HCFC-235cb) with hydrogen ($H_2$) in a reaction zone in the presence of a catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof, to produce HFC-1234yf, wherein the mole ratio of $H_2$ to the HCFC-235cb fed to the reaction zone is between about 1:1 and about 4:1.

The present invention also provides another process for making HFC-1234yf. This process comprises (a) reacting HCFC-235cb with $H_2$ in the presence of a catalytically effective amount of hydrogenation catalyst to form $CH_3CF_2CF_3$ (HFC-245cb); and (b) dehydrofluorinating HFC-245cb from (a) to form HFC-1234yf.

The present invention also provides another process for making HFC-1234yf. This process comprises (1) dehydrofluorinating HCFC-235cb in the presence of a catalytically effective amount of dehydrofluorination catalyst to form CHCl=$CFCF_3$ (HCFC-1224yd); and (2) hydrogenating CHCl=$CFCF_3$ from (1) in the presence of a hydrogenation catalyst comprising a catalytically effective amount of palladium supported on a support selected from the group consisting of chromium oxide, fluorinated chromium oxide, chromium fluoride, aluminum oxide, aluminum fluoride, fluorinated alumina, and mixtures thereof to form HFC-1234yf.

The present invention also provides a process for making $CH_2ClCF_2CF_3$ (HCFC-235cb). The process comprises reacting $CH_2ClF$ (HCFC-31) with $CF_2$=$CF_2$ (TFE) in a reaction zone in the presence of a catalytically effective amount of an aluminum halide composition having a bulk formula of $AlCl_xBr_yF_{3-x-y}$, wherein the average value of x is 0 to 3, the average value of y is 0 to 3-x, provided that the average values of x and y are not both 0.

The present invention also provides a composition comprising (a) $CF_3CF$=$CHCl$ and (b) HF; wherein the HF is present in an effective amount to form an azeotropic combination with $CF_3CF$=$CHCl$.

DETAILED DESCRIPTION

The present invention provides a process for making HFC-1234yf by reacting HCFC-235cb with hydrogen in a reaction zone over a suitable catalyst.

HCFC-235cb can be prepared from a variety of starting materials. For example, HCFC-235cb can be prepared by the reaction of potassium chloride with p-$CH_3C_6H_4SO_2CH_2C_2F_5$ as reported by McBee, et. al. in Journal of the American Chemical Society, Volume 77, pages 3149-3151 (1955).

Alternatively, the present invention provides a process for making HCFC-235cb. The process comprises reacting HCFC-31 with TFE in a reaction zone in the presence of an aluminum halide composition having a bulk formula of $AlCl_xBr_yF_{3-x-y}$, wherein the average value of x is 0 to 3, the average value of y is 0 to 3-x, provided that the average values of x and y are not both 0. It has been found in accordance with this invention that the HCFC-235cb can be produced with high selectivity.

Of note are embodiments wherein x is from about 0.10 to 3.00 and y is 0. Aluminum halide compositions of this type are known; see U.S. Pat. Nos. 5,157,171 and 5,162,594. In some cases HCFC-31 may be employed in the formation of the aluminum halide composition. Thus, in some embodiments, use of sufficient excess of HCFC-31 enables the production of $AlCl_xF_{3-x}$ in situ from anhydrous aluminum chloride so that a fluorine-containing catalyst is obtained.

The addition reaction involving HCFC-31 and TFE is based on a stoichiometry of 1 mole of HCFC-31 per mole of TFE. However, an excess of either reactant may be used as desired. Typically, the mole ratio of TFE to HCFC-31 is about 1.5 or less (e.g., from about 0.3:1 to about 1.1:1).

The process can be conducted batchwise or in a continuous manner. In the continuous mode, a mixture of HCFC-31 and TFE may be passed through or over a bed or body of the aluminum halide composition (which may be under agitation) at suitable temperature and pressure to form a product stream, and the desired products (e.g., HCFC-235cb) may be recovered from the stream by conventional methods such as fractional distillation.

In the batch process, the reactants and the aluminum halide composition may be combined in a suitable reactor to form a reaction mixture, and the mixture held at a suitable temperature and pressure (normally under agitation) until a desired degree of conversion is obtained. In one embodiment, the reactor is initially charged with the aluminum halide composition, and optionally with a diluent, and the HCFC-31 and TFE are fed in the desired mole ratio (as separate streams or as a combined stream) into the reactor and maintained therein until the reaction is substantially complete. If the reactor is fed with HCFC-31 and the aluminum halide composition prior to the substantial absence of the TFE, the reactor and ingredients is preferably kept relatively cold (e.g., between about $-78°$ C. and $10°$ C.) to discourage disproportionation of the HCFC-31 to fluorine-substituted methanes having a different fluorine content.

The process may be practiced with or without a solvent or diluent for the HCFC-31 and TFE. Typically, the HCFC-31 and TFE are diluted; however, the diluent may be primarily the HCFC-235cb produced in the addition reaction. Solvents which may be used include chlorocarbons (e.g., and $CCl_4$), hydrochlorofluorocarbons (e.g., $CHCl_2CF_3$ and mixtures of dichloropentafluoropropanes such as $CHCl_2C_2F_5$ and $CHClCF_2CClF_2$), and chlorofluorocarbons (e.g., $CClF_2CClF_2$), and mixtures thereof.

The addition reaction zone temperature is typically in the range of from about $0°$ C. to about $100°$ C. Of note are embodiments wherein the addition reaction zone temperature is in the range of from about $20°$ C. to about $80°$ C.

The reaction pressure may vary widely but normally the reaction is carried out at elevated pressures, particularly pressures generated autogenously in conformity with the reaction temperature employed. The pressure may be adjusted by controlling the amount of unreacted HCFC-31 and TFE.

At normally employed temperatures, the reaction time is typically between about 0.2 hour and 12 hours.

The amount of aluminum halide composition employed is typically in the range of from about 1 to 20 weight percent, based on the weight of the HCFC-31 reactant.

The effluent from the reaction zone (continuous or batch) typically includes HCFC-235cb, unreacted HCFC-31 and/or TFE, other HCFC-235 isomers such as $CH_2FCF_2CClF_2$. The effluent may also include one or more by-products such as $CH_2Cl_2$ and $CH_2ClCF_2CClF_2$. The reaction products may be recovered from the reaction zone by use of conventional means such as filtration and/or distillation. In batch mode, it is normally convenient to separate the reaction products from the aluminum halide composition and to use the separated aluminum halide composition in subsequent reactions.

Catalysts suitable for carrying out the process of making HFC-1234yf from HCFC-235cb in accordance with this invention comprise palladium and may optionally comprise additional Group VIII metals (e.g., Pt, Ru, Rh or Ni). The palladium is supported on chromium oxide, fluorinated chromium oxide, chromium fluoride, aluminum oxide, aluminum fluoride, fluorinated alumina, and mixtures thereof. The palladium-containing precursor used to prepare the catalyst is preferably a palladium salt (e.g., palladium chloride). Other metals, when used, may be added to the support during the preparation of the catalyst.

The supported metal catalysts may be prepared by conventional methods known in the art such as by impregnation of the carrier with a soluble salt of the catalytic metal (e.g., palladium chloride or rhodium nitrate) as described by Satterfield on page 95 of Heterogenous Catalysis in Industrial Practice, $2^{nd}$ edition (McGraw-Hill, New York, 1991).

By a catalytically effective amount is meant the concentration of catalysts on the support that is sufficient to carry out the catalytic reaction. The concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight based on the weight of the total metals present on the support.

The relative amount of hydrogen fed during contact of HCFC-235cb in a reaction zone containing the palladium-containing catalyst is from about 1 mole of $H_2$ per mole of HCFC-235cb to about 4 moles of $H_2$ per mole of HCFC-235cb, preferably from about 1 mole of $H_2$ per mole of HCFC-235cb to about 3 moles of $H_2$ per mole of $CH_2ClC_2F_5$ and more preferably from about 1 mole of $H_2$ per mole of $CH_2ClC_2F_5$ to about 2 moles $H_2$ per mole of $CH_2ClC_2F_5$.

The reaction zone temperature for the catalytic hydrogenation of HCFC-235cb is typically in the range of from about $100°$ C. to about $400°$ C., and preferably is in the range of from about $125°$ C. to about $350°$ C. The contact time is typically in the range of from about 1 to about 450 seconds, and preferably is in the range of from about 10 to about 120 seconds. The reactions are typically conducted at near atmospheric pressure.

The effluent from the reaction zone typically includes includes HCl, unreacted hydrogen, HF, $CF_3CF=CH_2$ (HFC-1234yf), as well as higher boiling products and intermediates typically including one or more of E- and Z-$CF_3CF=CHCl$ (HCFC-1224yd), $CF_3CHFCH_2Cl$ (HCFC-244eb), $CF_3CF_2CH_3$ (HFC-245cb), and any unconverted HCFC-235cb.

The HFC-1234yf present in the effluent from the reaction zone may be separated from the other components of the product mixture and unreacted starting materials by conventional means (e.g., distillation) and recovered. When HF is present in the effluent, this separation can also include isolation of azeotrope or near azeotrope composition of HFC-1234yf and HF and further processing to produce HF-free HFC-1234yf by using procedures similar to that disclosed in U.S. Patent Application Publication US2006/0106263(A1) which is incorporated herein by reference in its entirety.

Of note are embodiments wherein HCFC-235cb is present in the product mixture and wherein said HCFC-235cb is recovered and recycled to the reaction zone. In another embodiment intermediate products such as HCFC-E/Z-1224yd, HCFC-244eb, and $CF_3CF_2CH_3$ (HFC-245cb) are recycled to the reaction zone.

The present invention also provides a process for making HFC-1234yf that comprises (a) reacting HCFC-235cb with $H_2$ in a reaction zone in the presence of a catalytically effective amount of hydrogenation catalyst to form HFC-245cb; and (b) dehydrofluorinating HFC-245cb from (a) to form HFC-1234yf. In step (a) of this process of the invention, HCFC-235cb is reacted with hydrogen in the presence of a hydrogenation catalyst. Hydrogenation catalysts suitable for use in this invention include catalysts comprising at least one catalytic metal component selected from the group consisting of iron, cobalt, rhodium, nickel, palladium, and platinum. Said catalytic metal component is typically supported on a carbonaceous carrier such as activated carbon or graphite.

Of note are carbon-supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Of particular note are palladium catalysts supported on carbon (see e.g., U.S. Pat. No. 5,523,501, the teachings of which are incorporated herein by reference). Also of particular note are palladium catalysts supported on three-dimensional matrix porous carbonaceous materials. Preparation of such three-dimensional matrix porous carbonaceous materials is disclosed in U.S. Pat. No. 4,978,649, incorporated herein by reference.

The relative amount of hydrogen contacted with HCFC-235cb is typically from about one mole of hydrogen per mole of HCFC-235cb to about 15 moles of $H_2$ per mole of the HCFC-235cb starting material. Suitable reaction temperatures are typically from about 100° C. to about 350° C., preferably from about 125° C. to about 300° C. The contact time is typically from about 1 to about 450 seconds, preferably from about 10 to about 120 seconds. The reactions are typically conducted at atmospheric pressure or superatmospheric pressure.

The effluent from the reaction zone typically includes HCl, unreacted hydrogen, unreacted HCFC-235cb, and HFC-245cb. In one embodiment of the invention, the HFC-245cb is isolated by separation processes known in the art such as distillation. The isolated HFC-245cb is then used for step (b) of the process.

In another embodiment of the invention, the HCFC-235cb is reacted with hydrogen in the presence of catalyst in a molar ratio of $H_2$ to HCFC-235cb of from about 1:1 to about 10:1; and, after separation of excess hydrogen and hydrogen chloride, the remaining effluent from the reaction zone is then sent directly to step (b) of the process.

Unreacted HCFC-235cb may be recycled to step (a) of the process.

In step (b) of the process of the invention, the HFC-245cb produced in step (a) is contacted with a dehydrofluorination catalyst in a reaction zone for time sufficient to convert at least a portion of the HFC-245cb to HFC-1234yf.

Typical dehydrofluorination reaction conditions and dehydrofluorination catalysts for step (b) are disclosed in U.S. Pat. No. 5,396,000, which is herein incorporated by reference in its entirety. Preferably, the dehydrofluorination catalyst comprises at least one catalyst selected from the group consisting of carbon, aluminum fluoride, fluorided alumina, and trivalent chromium oxide.

Other dehydrofluorination catalysts useful for converting $C_3H_3F_5$ from step (a) to HFC-1234 products are described in U.S. Pat. No. 6,093,859; the teachings of this disclosure are incorporated herein by reference. Still other dehydrofluorination catalysts suitable for use in step (b) are described in U.S. Pat. No. 6,369,284; the teachings of this disclosure are incorporated herein by reference.

The present invention also provides another process for making HFC-1234yf. This process comprises (1) dehydrofluorinating HCFC-235cb in the presence of a catalytically effective amount of dehydrofluorination catalyst to form $CHCl=CFCF_3$ (HCFC-1224yd); and (2) hydrogenating $CHCl=CFCF_3$ from (a) to form HFC-1234yf. HCFC-1224yd may exist as one of two configurational isomers, E or Z. HCFC-1224yd as used herein refers to either E-HFC-1224yd or Z-HCFC-1224yd, as well as any combination or mixture of such isomers.

Dehydrofluorination in step (1) can be carried out in a manner similar to that described for step (b) above. Effluent from the dehydrofluorination step (1) includes HF and HCFC-1224yd. The HCFC-1224yd may be separated from HF, unconverted HCFC-235cb, and other by-products prior to step (2). The consideration of a process for the separation of HFC-1224yd from the product mixture by distillation includes the azeotropic combination thereof with HF. Of note are embodiments where the azeotrope of HCFC-1224yd and HF is directed to step (2). Also of note are embodiments wherein at least a portion of the azeotrope of HCFC-1224yd and HF is directed to a fluorination reaction zone (typically containing a fluorination catalyst such as chromium oxide) wherein HCFC-1224yd and HF are reacted together to form $CF_3CHFCHClF$ and/or $CF_3CF=CHF$.

As noted above, the present invention also provides azeotrope compositions comprising an effective amount of hydrogen fluoride combined with HFC-1224yd.

By effective amount is meant an amount, which, when combined with HFC-1224yd, results in the formation of azeotrope mixture. As recognized in the art, an azeotrope composition is a constant boiling liquid admixture of two or more different substances, wherein the admixture distills without substantial composition change and behaves as a constant boiling composition. Constant boiling compositions that are characterized as azeotropic, exhibit either a maximum or a minimum boiling point, as compared with that of the non-azeotropic mixtures of the same substances. Azeotropic compositions as used herein include homogeneous azeotropes, which are liquid admixtures of two or more substances that behave as a single substance, in that the vapor, produced by partial evaporation or distillation of the liquid, has the same composition as the liquid. Azeotropic compositions as used herein, also includes heterogeneous azeotropes where the liquid phase splits into two or more liquid phases. In these embodiments, at the azeotropic point, the vapor phase is in equilibrium with two liquid phases and all three phases have different compositions. If the two equilibrium liquid phases of a heterogeneous azeotrope are combined and the composition of the overall liquid phase calculated, this would be identical to the composition of the vapor phase.

Accordingly, the essential features of an azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope composition is subjected to boiling at different pressures. Thus, an azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

In accordance with this invention, compositions are provided which comprise the HCFC-1224yd and HF, wherein the HF is present in an effective amount to form an azeotropic combination with the HCFC-1224yd. According to calculations, these compositions comprise from about 78 mole percent to about 54 mole percent HF and from about 22 mole percent to about 46 mole percent HCFC-1224yd (which form azeotropes boiling at a temperature of from between about −25° C. and about 100° C. and at a pressure of from between about 4 psi (27 kPa) and about 295 psi (2034 kPa).

Compositions may be formed that consist essentially of azeotrope combinations of hydrogen fluoride with HCFC-1224yd. These include compositions calculated to consist essentially of from about 78 mole percent to about 54 mole percent HF and from about 22 mole percent to about 46 mole percent HCFC-1224yd (which form azeotropes boiling at a temperature of from between about −25° C. and about 100° C. and at a pressure of from between about 4 psi (27 kPa) and about 295 psi (2034 kPa).

Azeotropic compositions of HF and HCFC-1224yd are useful as sources of HF in fluorination reactions. For example by combining the azeotrope of HF and HCFC-1224yd with fluorination precursor compounds it is possible to obtain HF-free HCFC-1224yd and a fluorinated product (see for example, U.S. Pat. No. 6,224,781).

Catalysts suitable for carrying out the hydrogenation in step (2) comprise palladium and may optionally comprise additional Group VIII metals (e.g., Pt, Ru, Rh or Ni). The palladium is supported on chromium oxide, fluorinated chromium oxide, chromium fluoride, alumina, fluorided alumina, aluminum fluoride or a mixture thereof. The palladium-containing precursor used to prepare the catalyst is preferably a palladium salt (e.g., palladium chloride). Other metals, when used, may be added to the support during the preparation of the catalyst.

The supported metal catalysts may be prepared by conventional methods known in the art such as by impregnation of the carrier with a soluble salt of the catalytic metal (e.g., palladium chloride) as described by Satterfield on page 95 of Heterogenous Catalysis in Industrial Practice, $2^{nd}$ edition (McGraw-Hill, New York, 1991). Palladium supported on alumina is available commercially. Another suitable procedure for preparing a catalyst containing palladium on fluorided alumina is described in U.S. Pat. No. 4,873,381, which is incorporated herein by reference.

By a catalytically effective amount is meant the concentration of catalysts on the support that is sufficient to carry out the catalytic reaction. The concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight based on the weight of the total metals present on the support.

The relative amount of hydrogen fed during contact of HCFC-1224yd in a reaction zone containing the palladium-containing catalyst is typically from about 1 mole of $H_2$ per mole of HCFC-1224yd to about 4 moles of $H_2$ per mole of, HCFC-1224yd, preferably from about 1 mole of $H_2$ per mole of HCFC-1224yd to about 3 moles of $H_2$ per mole of HCFC-1224yd and more preferably from about 1 mole of $H_2$ per mole of HCFC-1224yd to about 2 moles $H_2$ per mole of HCFC-1224yd.

The reaction zone temperature for the catalytic hydrogenation of HCFC-1224yd is typically in the range of from about 100° C. to about 400° C., and preferably is in the range of from about 125° C. to about 350° C. The contact time is typically in the range of from about 1 to about 450 seconds, and preferably is in the range of from about 10 to about 120 seconds. The reactions are typically conducted at near atmospheric pressure.

The effluent from the reaction zone typically includes includes HCl, unreacted hydrogen, HFC-1234yf, as well as higher boiling products and intermediates typically including one or more of E- and Z-HCFC-1224yd and HCFC-244eb.

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific Examples are to be construed as merely illustrative, and do not constrain the remainder of the disclosure in any way whatsoever.

EXAMPLES

| LEGEND | |
| --- | --- |
| 215aa is $CF_3CCl_2CClF_2$ | 215cb is $CF_3CF_2CCl_3$ |
| 216cb is $CCl_2FCF_2CF_3$ | 225ca is $CHCl_2CF_2CF_3$ |
| 235cb is $CH_2ClCF_2CF_3$ | 235cc is $CH_2FCF_2CClF_2$ |
| 244 is $C_3H_3ClF_4$ | 245cb is $CF_3CF_2CH_3$ |
| 254eb is $CF_3CHFCH_3$ | 263fb is $CF_3CH_2CH_3$ |
| 1234yf is $CF_3CF{=}CH_2$ | |

Example 1

Reaction of Chlorofluoromethane and Tetrafluoroethylene

A 400 mL Hastelloy™ C shaker tube was charged with $AlCl_3$ (1.6 g, 0.012 mole) and 20 g of a mixture of dichloropentafluoropropanes as a reaction solvent. The tube was cooled to −78° C., evacuated, purged with nitrogen three times, and then charged with HCFC-31 (20.6 g, 0.30 mole). The tube was then placed in a barricaded shaker and charged with TFE (10.0 g, 0.10 mole). The temperature in the tube was increased to 39° C. Additional TFE was added (10.0 g, 0.20 mole total charge) and the temperature increased to 50° C. and held at 50° C. for six hours. The pressure in the tube decreased from a maximum of 176 psig (1315 kPa) to 65 psig (549 kPa). The resulting product mixture weighed 41.2 grams. Analysis of the product by $^1H$ NMR indicated the major products as shown in TABLE 1.

TABLE 1

| Component | Mole % |
| --- | --- |
| $CH_2ClCF_2CF_3$ | 31.9 |
| $CH_2FCF_2CClF_2$ | 3.3 |
| $CH_2ClCF_2CClF_2$ | 2.8 |
| $CH_2Cl_2$ | 26.9 |
| $C_3HCl_2F_5$ Isomers | 35.2 |

Hydrodechlorination of HCFC-235cb over fluorided $Pt/Al_2O_3$ catalyst is demonstrated by the following prophetic example.

Example 2

Hydrodechlorination of HCFC-235cb Over Fluorided $Pt/Al_2O_3$ Catalyst

A commercial platinum on aluminum oxide catalyst (5% $Pt/Al_2O_3$, 10 cc, 9.42 g, 12-20 mesh (1.68-0.84 mm)) is placed in a 30.5 cm×1.27 cm o.d. Hastelloy® tube. The tube is connected to a reactor system surrounded with an electrically-heated furnace. The catalyst is first dried for three hours under a nitrogen purge (25 sccm, 4.2×10$^{-7}$ m$^3$/s) as the temperature of the furnace is increased to 300° C. After cooling the reactor to 150° C., hydrogen gas (20 sccm, 3.3×10$^{-7}$ m$^3$/s) is passed into the reactor for three hours as the temperature in the reactor is increased to 300° C. After cooling the reactor to 150° C. under a flow of nitrogen (20 sccm, 3.3×10$^{-7}$ m$^3$/s), the catalyst is then fluorinated with a mixture of nitrogen and hydrogen fluoride according to the following sequence (time in hours, flow rate nitrogen, flow rate HF, temperature): 2 hours with N$_2$ flow of 7.5×10$^{-7}$ m$^3$/s, and HF flow of 8.3×10$^{-8}$ m$^3$/s at 150° C.; 2 hours with N$_2$ flow of 6.6×10$^{-7}$ m$^3$/s, and HF flow of 1.7×10$^{-7}$ m$^3$/s at 150° C.; 2 hours with N$_2$ flow of 6.6×10$^{-7}$ m$^3$/s, and HF flow of 1.7×10$^{-7}$ m$^3$/s at 200° C.; 2 hours with N$_2$ flow of 6.6×10$^{-7}$ m$^3$/s, and HF flow of 1.7×10$^{-7}$ m$^3$/s at 250° C.; 2 hours with N$_2$ flow of 4.2×10$^{-7}$ m$^3$/s, and HF flow of 4.2×10$^{-7}$ m$^3$/s at 250° C. The flow of hydrogen fluoride is then stopped and the reactor is purged with nitrogen.

A mixture of hydrogen and CF$_3$CF$_2$CH$_2$Cl (HCFC-235cb) in a 3:1 molar ratio is fed to the above catalyst at 250° C. with a contact time of 30 seconds. A typical analysis of the reactor effluent as may be determined by GC-MS is given in TABLE 2.

TABLE 2

| EX. No. | GC Area Percentage | | | |
|---|---|---|---|---|
| | HFC-245cb | HFC-263fb | HFC-254eb | HCFC-235cb |
| 2 | 92 | 4 | 3 | 1 |

What is claimed is:

1. A process for making CH$_2$ClCF$_2$CF$_3$, comprising:
   reacting CH$_2$ClF with CF$_2$=CF$_2$ in a reaction zone in the presence of a catalytically effective amount of an aluminum halide composition having a bulk formula of AlCl$_x$Br$_y$F$_{3-x-y}$ wherein the average value of x is 0 to 3, the average value of y is 0 to 3-x, provided that the average values of x and y are not both 0.

2. A composition comprising:
   (a) CF$_3$CF=CHCl; and
   (b) HF; wherein the HF is present in an effective amount to form an azeotropic combination with CF$_3$CF=CHCl.

3. The azeotropic composition of claim 2, comprising from about 22 to about 46 mole percent CF$_3$CF=CHCl and HF.

4. The azeotropic composition of claim 2, comprising from about 22 to about 46 mole percent CF$_3$CF=CHCl and HF, wherein the vapor pressure is from about 4 psia to about 295 psi at a temperature of from about −25° C. to about 100° C.

5. The azeotropic composition of claim 2, wherein said composition consists essentially of from about 22 to about 46 mole percent CF$_3$CF=CHCl and HF, wherein the vapor pressure is from about 4 psia to about 25 psi at a temperature of from about −25° C. to about 100° C.

6. The process of claim 1, x is from 0.1 to 3.0 and y is 0.

7. The process of claim 1, wherein the mole ratio of CF$_2$=CF$_2$ to CH$_2$CFCl is 1.5 or less.

8. The process of claim 7, wherein the mole ratio of CF$_2$=CF$_2$ to CH$_2$CFCl is from about 0.3:1 to about 1.1:1.

* * * * *